US00PP22081P2

(12) United States Plant Patent
Podaras

(10) Patent No.: US PP22,081 P2
(45) Date of Patent: Aug. 16, 2011

(54) ***BUDDLEJA* PLANT NAMED 'PODARAS #3'**

(50) Latin Name: *Buddleja marubiafolia×Buddleja alternifolia*
Varietal Denomination: Podaras #3

(75) Inventor: Peter Podaras, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/660,666

(22) Filed: Mar. 2, 2010

(51) Int. Cl.
*A01H 5/00* (2006.01)

(52) U.S. Cl. ..... Plt./242

(58) Field of Classification Search ..... Plt./242
See application file for complete search history.

*Primary Examiner* — Susan B McCormick Ewoldt
(74) *Attorney, Agent, or Firm* — C. A. Whealy

(57) ABSTRACT

A new and distinct cultivar of *Buddleja* plant named 'Podaras #3', characterized by its upright to outwardly spreading plant habit; freely flowering habit; sterile orange-colored flowers; and good garden performance.

1 Drawing Sheet

Botanical designation: *Buddleja marubiafolia×Buddleja alternifolia.*

Cultivar denomination: 'PODARAS #3'.

BACKGROUND OF THE INVENTION

The present invention relates to a new and distinct cultivar of *Buddleja* plant, botanically known as *Buddleja marubiafolia×Buddleja alternifolia* and hereinafter referred to by the name 'Podaras #3'.

The new *Buddleja* plant is a product of a planned breeding program conducted by the Inventor in Ithaca, N.Y. The objective of the breeding program was to create new compact and sterile *Buddleja* plants with unique and attractive flower coloration.

The new *Buddleja* plant originated from a cross-pollination on Jun. 15, 2006 in Ithaca, N.Y., of an unnamed selection of *Buddleja marubiafolia*, not patented, as the female, or seed, parent with an unnamed selection of *Buddleja alternifolia*, not patented, as the male, or pollen, parent. The new *Buddleja* plant was discovered and selected by the Inventor as a single flowering plant within the progeny of the stated cross-pollination in a controlled environment in Ithaca, N.Y. in September, 2006.

Asexual reproduction of the new *Buddleja* plant by cuttings in a controlled greenhouse environment in West Chicago, Ill. since February, 2008, has shown that the unique features of this new *Buddleja* plant are stable and reproduced true to type in successive generations.

SUMMARY OF THE INVENTION

Plants of the new *Buddleja* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Podaras #3'. These characteristics in combination distinguish 'Podaras #3' as a new and distinct *Buddleja* plant:

1. Upright to outwardly spreading plant habit.
2. Freely flowering habit.

3. Sterile orange-colored flowers.
4. Good garden performance.

Plants of the new *Buddleja* differ from plants of the female parent selection in the following characteristics:

1. Plants of the new *Buddleja* are more vigorous and larger than plants of the female parent selection.
2. Plants of the new *Buddleja* have larger flowers than plants of the female parent selection.
3. Flowers of plants of the new *Buddleja* are sterile whereas flowers of plants of the female parent selection are fertile.
4. Plants of the new *Buddleja* are more cold tolerant than plants of the female parent selection, Plants of the new *Buddleja* differ from plants of the male parent selection in the following characteristics:

1. Plants of the new *Buddleja* have opposite leaves whereas plants of the male parent selection have alternate leaves.
2. Plants of the new *Buddleja* flower for a longer period of time than plants of the male parent selection.
3. Plants of the new *Buddleja* and the male parent selection differ in flower color as plants of the male parent selection have light pink-colored flowers.

Plants of the new *Buddleja* can be compared to plants of *Buddleja weyeriana* 'Honeycomb', not patented. In side-by-side comparisons, plants of the new *Buddleja* and 'Honeycomb' differed in the following characteristics:

1. Plants of the new *Buddleja* were denser and more vigorous than plants of 'Honeycomb'.
2. Plants of the new *Buddleja* have smaller leaves than plants of 'Honeycomb'.
3. Plants of the new *Buddleja* and 'Honeycomb' differed in flower color as plants of 'Honeycomb' had yellow-colored flowers.
4. Flowers of plants of the new *Buddleja* were sterile whereas flowers of plants of 'Honeycomb' were fertile.

BRIEF DESCRIPTION OF THE PHOTOGRAPHS

The accompanying colored photographs illustrate the overall appearance of the new *Buddleja* plant, showing the colors as true as it is reasonably possible to obtain in colored reproductions of this type. Colors in the photographs may differ slightly from the color values cited in the detailed botanical description which accurately describe the colors of the new *Buddleja* plant.

The photograph at the bottom of the sheet comprises a side perspective view of a typical flowering plant of 'Podaras #3' grown in a container.

The photograph at the top of the sheet is a close-up view of a typical inflorescence of 'Podaras #3'.

DETAILED BOTANICAL DESCRIPTION

The aforementioned photographs and following observations, measurements and values describe plants grown in Arroyo Grande, Calif. under commercial practice during the summer in 12.5-cm containers in a polyethylene-covered greenhouse with day temperatures averaging 21° C. and night temperatures averaging 7° C. Plants were pinched two times and were one year old when the photographs and description were taken. In the following description, color references are made to The Royal Horticultural Society Colour Chart, 2007 Edition, except where general terms of ordinary dictionary significance are used.

Botanical classification: *Buddleja marubiafolia*×*Buddleja alternifolia* 'Podaras #3'.

Parentage:

*Female, or seed, parent.*—Unnamed selection of *Buddleja marubiafolia*, not patented.

*Male, or pollen, parent.*—Unnamed selection of *Buddleja alternifolia*, not patented.

Propagation:

*Type.*—By cuttings.

*Time to initiate roots plant, summer.*—About 21 days at temperatures of 18° C. to 24° C.

*Time to initiate roots plant, winter.*—About 25 to 30 days at temperatures of 18° C. to 24° C.

*Time to produce a rooted plant, summer.*—About 40 days at temperatures of 18° C. to 24° C.

*Time to produce a rooted plant, winter.*—About 45 days at temperatures of 18° C. to 24° C.

*Root description.*—Fibrous, fine; white in color.

*Rooting habit.*—Freely branching; moderately dense.

Plant description:

*Plant form/habit.*—Deciduous perennial shrub; upright and outwardly spreading habit; broad inverted triangle; vigorous growth habit.

*Plant height.*—About 47 cm.

*Plant width (spread).*—About 56 cm by 62 cm.

*Lateral branches.*—Quantity: About eight main branches per plant. Length: About 50 cm. Diameter: About 6 mm. Internode length: About 3 cm. Strength: Strong. Texture, developing stems: Lanulose. Texture, mature stems: Smooth, glabrous. Color, developing: Close to 190C. Color, mature: Close to N199B.

Foliage description:

*Arrangement*—Opposite, simple.

*Length.*—About 4.8 cm to 5 cm.

*Width.*—About 2 cm.

*Shape.*—Elliptical.

*Apex.*—Acute.

*Base.*—Attenuate.

*Margin.*—Nearly entire to irregularly dentate.

*Texture, upper and lower surfaces.*—Pubescent.

*Venation pattern.*—Pinnate, reticulate.

*Color.*—Developing leaves, upper surface: Close to 191A. Developing leaves, lower surface: Close to 190A. Fully expanded leaves, upper surface: Close to 137B; venation, close to 147C. Fully expanded leaves, lower surface: Close to 147B; venation, close to 148D.

*Petiole.*—Length: About 3 mm. Diameter: About 2 mm. Texture, upper and lower surfaces: Pubescent. Color, upper surface: Close to 194B. Color, lower surface: Close to 194D.

Flower description:

*Flower type/habit.*—Single rotate and salverform flowers arranged in compound terminal and axillary panicles; flowers face upright and outward; panicles roughly globular to oval in shape; freely flowering habit with about 32 flower buds and flowers developing per inflorescence.

*Fragrance.*—Faintly fragrant; sweet.

*Natural flowering season.*—Plants begin flowering about three months after planting; flowering continuous from spring until frost in California.

*Postproduction longevity.*—Flowers last about three to four days on the plant; flowers persistent.

*Flower buds.*—Height: About 8 mm. Diameter: About 2.5 mm. Shape: Oblong. Color: Close to 17B.

*Inflorescence height.*—About 2 cm.

*Inflorescence diameter.*—About 2 cm.

*Flower diameter.*—About 6 mm.

*Flower depth.*—About 1.1 cm.

*Flower throat, diameter.*—About 1.5 mm.

*Flower tube, length.*—About 8 mm.

*Flower tube, diameter at base.*—About 2 mm.

*Petals.*—Quantity per flower: Typically four in a single whorl; petals fused into a narrow tube. Lobe length: About 2.5 mm. Lobe width: About 2.5 mm. Lobe shape: Roughly spatulate. Lobe apex: Rounded. Lobe margin: Entire. Texture, upper and lower lobe surfaces: Smooth, glabrous. Texture, throat: Slightly pubescent. Texture, tube: Sparsely pubescent. Color: Developing petals, upper surface: Close to 16A to 16B. Developing petals, lower surface: Close to 16C. Fully expanded petals, upper surface: Close to 24A; venation, close to 24A; color becoming closer to 26A with development. Fully expanded petals, lower surface: Close to 24B to 24C; venation, close to 24C. Throat: Close to 25A; venation, close to 25A. Tube: Close to 29B; venation, close to 29B.

*Sepals.*—Quantity per flower: Typically four in a single whorl, fused towards the base; campanulate calyx. Length: About 2 mm. Width: About 1 mm. Shape: Lanceolate. Apex: Acute. Margin: Entire. Texture, upper surface: Smooth, glabrous. Texture, lower surface: Pubescent. Color, upper surface: Close to 144A. Color, lower surface: Close to 193C.

*Peduncles.*—Length: About 1.8 cm. Diameter: About 1.5 mm. Angle: Erect to about 45° from vertical. Strength: Moderately strong. Texture: Tomentose. Color: Close to 192C.

*Pedicels.*—Length: About 3 mm. Diameter: About 1 mm. Angle: About 45° from peduncle axis. Strength: Moderately strong. Texture: Tomentose. Color: Close to 192C.

*Reproductive organs.*—Stamens: Quantity per flower: Typically four; filaments adnate to the corolla tube. Filament length: About 2.5 mm. Filament color: Close to 4C. Anther shape: Lanceolate. Anther length: About 1 mm. Anther color: Close to N199A. Pollen amount: None. Pistils: Quantity per flower: One. Pistil length: About 4 mm. Stigma shape: Oval. Stigma color: Close to 144A. Style length: About 2 mm. Style color: Close to 145C. Ovary color: Close to 146B.

*Seed/fruit.*—Flowers of plants of the new *Buddleja* are sterile and seed and fruit development have not been observed.

Disease/pest resistance: Plants of the new *Buddleja* have been not been observed to be resistant to pathogens and pests common to *Buddleja.*

Garden performance: Plants of the new *Buddleja* have been observed to have good garden performance and tolerate rain, wind and temperatures ranging from about 0° C. to about 40° C.

It is claimed:

1. A new and distinct *Buddleja* plant named 'Podaras #3' as illustrated and described.

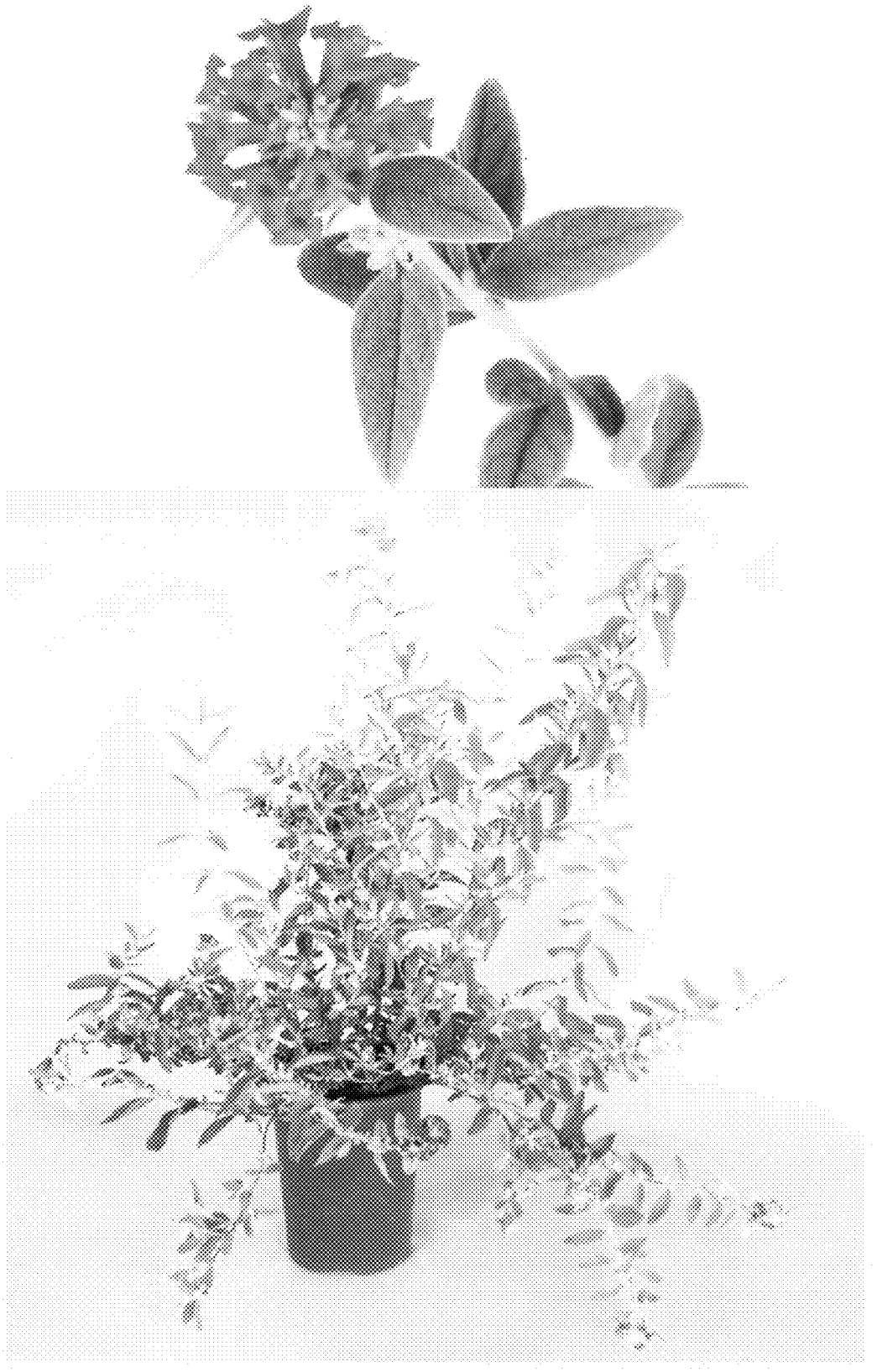

* * * * *